US006322813B1

United States Patent
Green et al.

(10) Patent No.: US 6,322,813 B1
(45) Date of Patent: *Nov. 27, 2001

(54) COMPACT MEMBER, METHOD OF MANUFACTURING AND USE THEREOF

(75) Inventors: Torkel Green; Christer Nyström, both of Uppsala (SE)

(73) Assignee: Pharmacia AB, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/960,805

(22) Filed: Oct. 30, 1997

Related U.S. Application Data

(60) Provisional application No. 60/031,723, filed on Nov. 25, 1996.

(30) Foreign Application Priority Data

Nov. 12, 1996 (SE) ..................................... 9604124

(51) Int. Cl.[7] ............................. A61K 9/22; A61K 47/38
(52) U.S. Cl. ........................................ 424/465; 424/488
(58) Field of Search .................................. 424/443, 465, 424/498

(56) References Cited

U.S. PATENT DOCUMENTS 3,593,855 * 7/1971 Stana ..................................... 210/500

5,607,695   3/1997   Ek et al. .

FOREIGN PATENT DOCUMENTS

WO9118590   12/1991   (WO) .
WO9119483   12/1991   (WO) .
WO9423704   10/1994   (WO) .

OTHER PUBLICATIONS

Fell et al, J. Pharm. Pharmacol., 20(1968), pp. 653–659.

Davidson et al, International Journal of Pharmaceutics, 100(1993), pp. 49–54.

* cited by examiner

*Primary Examiner*—Peter F. Kulkosky
(74) *Attorney, Agent, or Firm*—Dinsmore & Shohl LLP

(57) ABSTRACT

The invention relates to a compact member comprising a plurality of porous cellulose matrices (PCMs), and providing extended release of an active compound located in the pores of said PCMs together with a release modifying agent. The friability of the compact member is less than 2.1%, and the disintegration time in-vitro of said compact member is less than 240 minutes. The compact member is manufactured by exposing a plurality of PCMs to an active compound and a release modifying agent, in optional sequence or mixture, for a time sufficient for said active compound and release modifying agent to fill the pores in said PCMs to a preselected level. The PCMs are subsequently compacted to a desired shape. The invention further relates to use of the compact members for administration of a drug.

21 Claims, 6 Drawing Sheets

US 6,322,813 B1

COMPACT MEMBER, METHOD OF MANUFACTURING AND USE THEREOF

This application claims benefit of provisional application No. 60/031,723, filed Nov. 25, 1996.

TECHNICAL FIELD OF THE INVENTION

The present invention relates to a compact member having extended release of an active compound. In particular it relates to a tablet based on multiple-units made of porous cellulose matrices (PCMs), and having the property of at the same time being easily handled without being damaged, and having an adequate rate of disintegration. The release rate of the active compound is controllable.

BACKGROUND OF THE INVENTION AND PRIOR ART

Simple incorporation of drugs into PCMs (without coating) may retard the drug release but usually not to an extent sufficient for extended release purposes, and has therefore not been commercially feasible.

Extended release of an active compound, e.g. a drug, is possible to achieve by providing drug-loaded porous beads with a coating, such as a release-controlling, water permeable film or membrane. This technique has been extensively used heretofore in the art. In the process of forming such films or membranes organic solvents are often needed, which from both economic and environmental point of view is undesirable.

Multiple-unit (MU) preparations containing a plurality of pellets have been used as carriers of drugs previously. The use of MU drug preparations is considered to promote good absorption properties since they are dispersed over a large area in the gastrointestinal (GI) tract. Furthermore, they are considered to have a lower transit rate especially in the colon compared to matrix tablets. In addition, MU preparations are preferable to single unit preparations, since they may be divided into smaller portions all having the same release and absorption properties which will give greater flexibility in selection of the dose size. Also, MU preparations will facilitate administration of the drug to patients having problems to swallow and will considerably reduce the risk of dose dumping.

Extended release multiple-units (MUs), based on porous matrices of the type mentioned above, as carriers of drugs have commonly been filled in hard gelatine capsules. However, there is an increasing interest in the compaction of extended release multiple-units into disintegrating tablets. The reason for this is the advantages of tablets over the above mentioned capsules, such as more rational production, higher dose accuracy and lower risk of tampering. Unfortunately the release rate is often affected by compaction. The release rate may increase due to crushing, formation of cracks in the release-controlling coating etc., or decrease due to complete or partial failure of tablets to disintegrate. Tablets made of coated multiple-units with intact or nearly intact release rate by the use of relatively large amounts of excipients have been reported. The function of the added excipients may be to protect the film by absorbing energy during compaction or to act as disintegrants.

PCMs may e.g. be prepared by a wet or a dry method as disclosed in International Patent Applications WO-A-91/18590 and WO-A-94/23703, respectively, both assigned to Pharmacia & Upjohn AB of Sweden. The preparation of PCMs does not form part of the invention, and will not be specifically discussed herein. Instead, the said patent applications are incorporated by reference. PCMs are normally small spherical particles, so-called pellets, with a diameter in the range of from about 0.5 up to about 1.5 mm, suitably with a diameter of about 1 mm.

Other methods for making pellets of cellulose, optionally incorporating one or more additional substances, e.g. lipids, could be extrusion/spheronization, "layering", melt-pelletization and spray-cooling.

Extrusion/spheronization is performed by pressing a moistured powder mass through a metal sheet wherein a plurality of holes has been made. The mass thereby forms spaghetti-like threads. These threads are transferred to a horizontally rotating plate, where they are broken to pieces and formed to spheres which subsequently are allowed to dry.

In "layering", powder and liquid are added to small seeds (commonly sugar), having been rotated in a so-called pan or the like. Layer by layer, larger spheres are built.

In melt-pelletization, spheres can be formed in a Teflon®-coated mixer when part of the powder melts.

In spray-cooling a melt is commninuted into small droplets that solidify and form small spheres.

The above methods are part of the prior art and the skilled man will be able to manufacture beads according to any of said routes by virtue of his ordinary skill.

Porous cellulose matrices (PCMs) have been shown to be potential multiple-unit (MU) drug carriers (Davidson et al., "Porous cellulose matrices—a novel excipient for the formulation of solid dosage forms", Int. J. Pharm. 100 (1993) 49–54).

A possible method to modify the drug release rate from non-compacted PCMs is by incorporating release-modifying substances together with the drug into the pores of the cellulose matrix, as disclosed in WO-A-91/18590.

If thermoplastic materials could be used as release modifiers, the incorporation could be done by making use of such materials in a molten state. It might then be possible that the process be carried out without excessive energy input or organic solvents. Especially if the drug could be incorporated by suspending it in or otherwise mix it with the melted release modifier, this process could be very cost effective.

Non-compacted PCMs have been shown to extend the release of paracetamol incorporated together with lipids in the matrix pores. This type of spherical extended release pellets could be produced very cost effectively with low energy consumption and without any organic solvents. Another possible advantage of this type of system is that drug release from matrix pellets of this type may be less sensitive to compression than pellets coated with a thin membrane. It also seems reasonable that the disintegrating effect of cellulose could be advantageous when trying to compact PCMs into disintegrating multiple-unit tablets.

As mentioned above, MUs are commonly delivered in doses contained in hard gelatine capsules. It would be desirable to be able to manufacture tablets by compression of MUs, because manufacture would thereby become more cost effective, tablets would be more easily divided in subdoses etc. However, MUs are difficult to make into tablets by compression since 1) tablets made from MUs do not easily disintegrate upon oral administration, and
2) the MUs are easily crushed or damaged during the compaction process, having as a consequence that the release rate is substantially increased.

In order to avoid the above problems the prior art teaches addition of substantial amounts of various additives, located between the particles. Such measures adds to the complexity and cost of the manufacturing process, apart from introducing unnecessary chemicals into the medicaments.

SUMMARY OF THE INVENTION

It is therefore an object of the invention to provide compact members (tablets) having extended release of an active compound, said compact members having the properties of
1) being easy to handle without said members being damaged; and
2) rapidly disintegrating in-vivo (in the gastrointestinal tract) e.g. when administered orally.

In addition, the above object should be achieved without having to incorporate large amounts of additives in the compact members.

This object is achieved in one aspect of the invention with a compact member comprising a plurality of PCMs, and providing extended release of an active compound contained therein.

The advantage of the compact member of the present invention is thus the combination of
1) it being easy to handle in industrial processes, such as packaging etc., by virtue of its low friability, and
2) disintegration times suitable for its intended purpose.

The compact member suitably contains talc. The release rate may be controlled by varying the talc content Thereby, the release rate of the active compound can be practically equal to the release rate of free PCMs.

Especially it is suited for use in its preferred embodiment as a tablet containing a drug.

In another aspect of the invention there is provided a method of manufacturing tablets having the desired properties.

In yet another aspect of the invention there is provided use of a compact member according to the present invention for administration of a drug, as defined in claim 20.

The invention will become more fully understood from the following illustrative description of preferred embodiments thereof, by way of non-limiting examples, and with reference to the appended drawing figures.

DETAILED DESCRIPTION OF THE INVENTION

Figure 1:
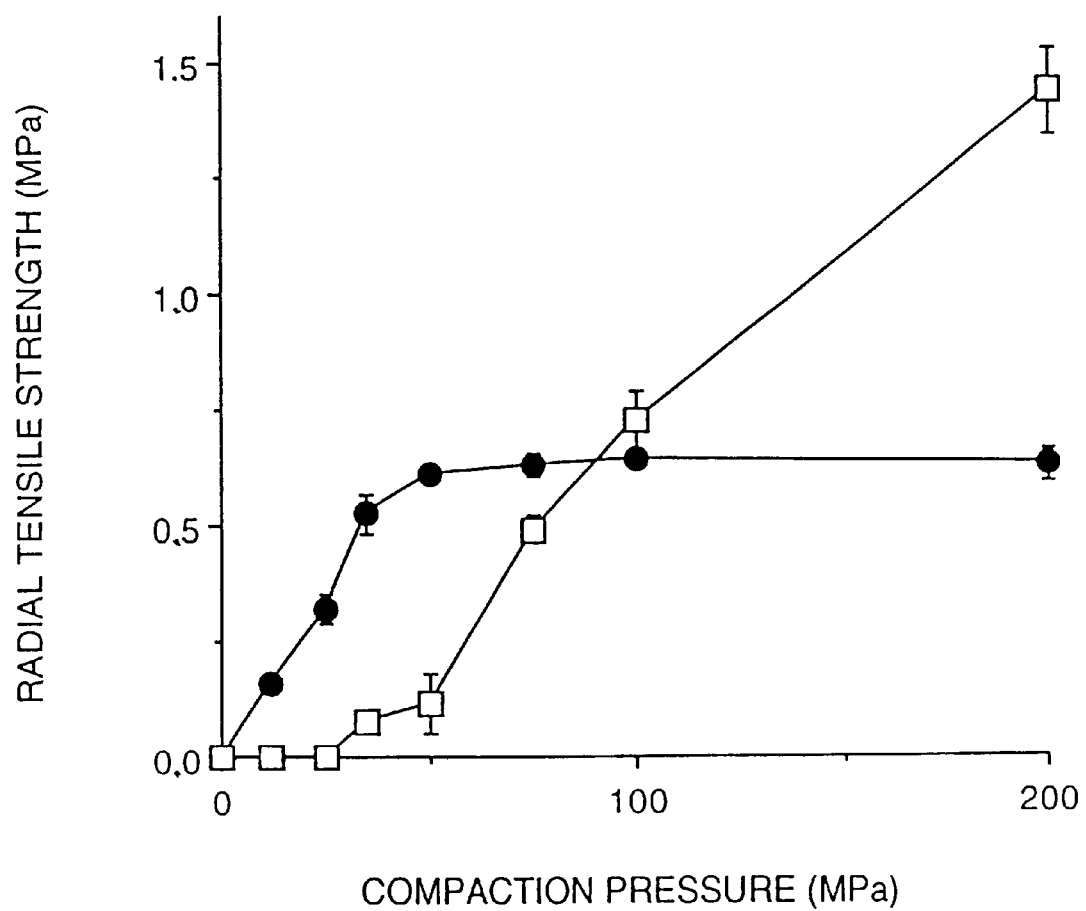
FIG. 1 is a graph showing radial tensile strength for tablets according to the invention as a function of compaction pressure.

Drug release from PCMs has, as mentioned above, been shown to be possible to extend over at least 16 hours by incorporating lipophilic release modifiers together with the drug into the pores in the cellulose matrix. The rate of release could be adjusted by varying the release modifier composition, drug concentration and particle size of the PCMs. The release seems to be controlled by diffusion from the matrix but is also affected by the distribution of drug in the matrices and an increase of porosity due to erosion of matrix material and pores formed by the swelling of cellulose. The incorporation of drug and release modifier could be performed simultaneously by dispersing a micronized drug into the molten release modifiers. Hence, an extended release multiple-unit preparation may be prepared from PCMs with a simple, solvent-free, one-step process.

Lipids may be suitable as release modifiers for incorporation into PCMs, since they are often low-melting, non-toxic, relatively inexpensive and there is a broad range of lipids with different physico-chemical properties.

Lipids may be classified on the basis of their different interaction with water into non-polar lipids (e.g. aliphatic hydrocarbons) and polar lipids. The polar lipids could be further subdivided into different classes: I) insoluble non-swelling amphiphilic lipids, II) insoluble swelling amphiphilic lipids and III) soluble amphiphilic lipids, where the solubility refers to water as a medium.

The release rate from lipophilic matrices can often be controlled by the use of a mixture of a nonpolar and a polar lipid or of two polar lipids from different classes.

There is no universal definition of "lipid". Lipids are sometimes defined as naturally occurring fats, oils and waxes. However, here the word lipid is used in a broader sense covering also e.g. aliphatic hydrocarbons and fatty alcohols. Examples of lipids which have been used as meltable excipients are fatty acids, e.g. stearic acid, long chain alcohols, e.g. cetostearyl alcohol, naturally occurring or synthetic waxes, glyceryl esters of fatty acids, e.g glyceryl monostearate, glyceryl distearate, or glyceryl tristearate, aliphatic hydrocarbons, e.g. hard paraffin, polyglycerol esters of fatty acids, and any mixture thereof.

In the present invention, it is advantageous to use a lipid with a melting point in the range of from about 10° C. up to about 200° C., suitably from 20° C. up to 150° C., and preferably 30° C. up to 100° C.

Prior to compaction, small amounts of additives may be added to the PCMs to give the resulting compact members specific properties as regards release rate, tensile strength etc. Thus, the compact members may contain up to about 10%, and preferably up to 5% by weight of talc. Also, the compact members may contain up to about 1%, and preferably up to 0.5% by weight of a lubricant. Suitably, use is made of magnesium stearate, which is a conventional and economic choice.

The active compounds contained in the compact members of the present invention, are preferably drugs (pharmaceuticals). The present invention is suitable for hydrophilic drugs, i.e. drugs soluble in water or aqueous solutions. Furthermore, the present invention is particularly useful for drugs exhibiting a biological half-life of less than about 20 hours, since extended release of drugs with a longer biological half-life is normally not necessary. The present invention is preferably used for drugs exhibiting a biological half-life of less than 15 hours, and more preferably less than 10 hours.

It should be recognized that the active compound to be incorporated in the compact members of the present invention may be any of a number of different compounds for different uses apart from drugs, e.g. fertilizers, pesticides, herbicides etc.

The compact members of the present invention may contain up to about 50% by weight of the active compound, suitably up to 10%, and preferably up to 2.5% by weight of the active compound.

In manufacturing of the compact members according to the present method, the PCMs can be exposed to the active compound and release-modifying agent in optional order, or preferably simultaneously, after premixing of the active compound and release-modifying agent. The active compound and release-modifying agent can be dry mixed, as disclosed in Example 1 of the present specification. Other types of mixing are conceivable, and for the purpose of this invention, the term mixing would encompass any form of dispersing, suspending, emulsifying etc. which reasonably homogeneously would distribute the active compound in a release-modifying agent.

In order not to obtain unacceptable agglomeration of individual PCMs because of an excess of active compound and release-modifying agent present, the amount of active compound and release-modifying agent necessary to fill the pores to a preselected level for a given batch, is calculated from the densities of the active compound and release-modifying agent and the known pore volume for a given amount of PCMs. The porosity of pure PCMs can be calculated from pellet density data measured by mercury porosimetry and from apparent density data obtained by helium pycnometry. In the present invention, it is suitable that the pores are filled with the active compound and release-modifying agent to at least about 50% of the pore volume, preferably at least 70%, and more preferably at least 80% of the pore volume, before compacting the PCMs.

In manufacturing of the compact members according to the present method, the PCMs comprising an active compound and a release-modifying agent are compacted to a desired shape. Examples of desired shapes of compact members are cylindrical, cylindrical with rounded upper and lower surfaces, cubical and essentially spherical.

In manufacturing of the compact members according to the present method, the pressure in the compacting step is suitably less than about 500 MPa, preferably in the range of from 10 up to 200 MPa, and more preferably in the range of from 50 up to 150 MPa.

From a medical point of view it is desirable that compact members, such as tablets, exhibit disintegration times in-vitro of less than about 240 minutes. The disintegration time in-vitro is suitably less than 90 minutes, and preferably less than 60 minutes.

Radial tensile strength is an important property for the compact members of the invention, since the radial tensil strength is a measure of the cohesive properties of the compact members, e.g. tablets. The radial tensile strength of the compact member of the present invention can be higher than about 0.1 MPa, suitably higher than 0.3 MPa, and preferably higher than 0.5 MPa

EXPERIMENTAL

The following Examples are provided for purposes of illustration only and are not to be construed as in any way limiting the scope of the present invention, which is defined by the appended claims.

The percentages and parts are per weight, unless otherwise stated.

Example 1 (not according to the invention)

A multiple-unit extended release matrix preparation, was prepared by the incorporation of a hydrophilic drug (Paracetamol; Hoechst, Germany) and lipophilic release modifiers (Cetanol; Bionord AB, Sweden, and hard paraffin; MB Sveda, Sweden) into porous cellulose matrices (PCMs).

The PCMs were made according to the method disclosed in WO-A-94/23703. The drug was micronized and dry mixed with a lipid, using a mortar and a pestle. The drug and lipid mixture was then heated on a water bath and the drug was thereby dispersed substantially homogeneously in the molten lipid. PCMs were added during stirring. It is also conceivable to add the drug to the molten lipid, or vice versa. The mixtures were allowed to cool during stirring. The size fractions 0.5–0.71, 0.71–1.2 and 1.2–1.4 mm were obtained by sieving. Two pellets with no cellulose were also prepared for comparison. The various formulations are shown in Table 1.

TABLE 1

Prepared pellets and results from linear regression of ln(released drug) vs ln(time) for <60% drug released for studied pellets. Lipid concentration is 43% (w/w) unless otherwise indicated.

| Lipid composition. (paraffin:cetanol) (% w/w) | Paracetamol content (% w/w) | Particle size (mm) | Drug particle size ($\mu$m) |
|---|---|---|---|
| 1:0 | 2.5 | 0.7–1.2 | 2.2 |
| 1:1 | 2.5 | 0.7–1.2 | 2.2 |
| 1:2 | 2.5 | 0.7–1.2 | 2.2 |
| 1:3 | 2.5 | 0.7–1.2 | 2.2 |
| 0:1 | 2.5 | 0.7–1.2 | 2.2 |
| 1:2 (40% lipid) | 2.5 | 0.7–1.2 | 2.2 |
| 1:2 (37% lipid) | 2.5 | 0.7–1.2 | 2.2 |
| 1:2 | 2.5 | 0.5–0.7 | 2.2 |
| 1:2 | 2.5 | 1.2–1.4 | 2.2 |
| 1:2 | 2.5 | 0.7–1.2 | 3.4 |
| 1:2 | 2.5 | 0.7–1.2 | 8.4 |
| 1:2 | 1 | 0.7–1.2 | 2.2 |
| 1:2 | 5 | 0.7–1.2 | 2.2 |

The amounts of drug incorporated into PCMs were assayed spectrophoto-metrically after extraction in ethanol (95%).

Figure 3:
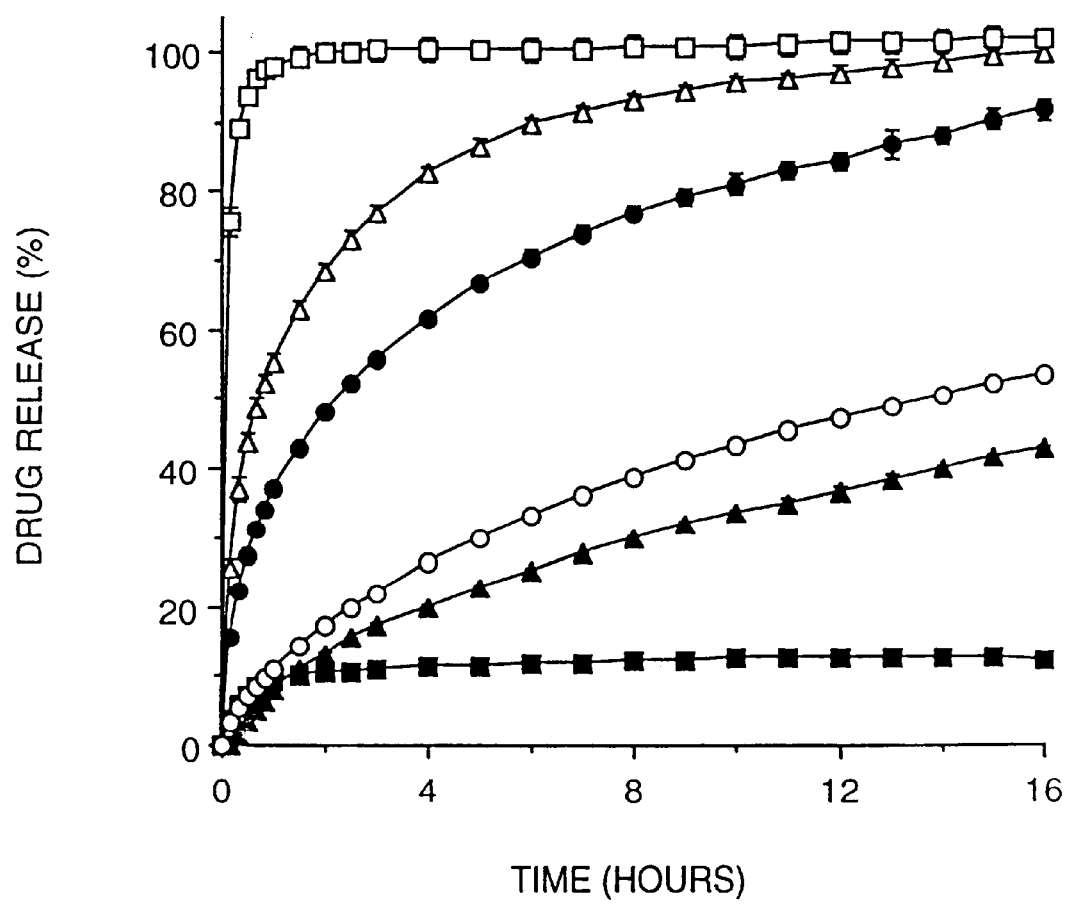
FIG. 3 is a graph showing release of drug from pellets not according to the invention as a function of time for different lipid compositions.

The release rates were determined according to USP method I (basket) in distilled water, at 37° C., 100 rpm. The amount released was detected spectrophotometrically ($\lambda$=244 nm). The amount of pellets was chosen in order to maintain sink condition during the entire release measurement and to get optimal analytical sensitivity. The results are shown in FIG. 3 as release of drug vs time for PCMs loaded with various lipid compositions. In FIG. 3 filled squares represent PCM and pure hard paraffin, filled triangles represent PCM and 1:1 of hard paraffin:cetanol, filled circles represent PCM and 1:2 of hard paraffin:cetanol, empty triangles represent PCM and 1:3 of hard paraffin:cetanol, empty squares represent PCM and pure cetanol, and empty circles represent reference pellets without cellulose matrix, i.e. pure lipid.

As can be seen in the figure, the in-vitro drug release could be extended over at least 16 hours. The release rate could be controlled by varying the ratio of cetanol to paraffin.

Example 2 (according to the invention)

The possibility to compact PCMs into disintegrating extended release multiple-unit tablets was studied using a hydrophilic drug and lipophilic release modifiers.

Paracetamol (Hoechst, Germany) was chosen as a model drug substance since it is relatively stable and non-toxic and since it has been used in earlier studies.

Cetanol (Bionord AB, Sweden) and hard paraffin (MB Sveda, Sweden) was used as release-modifying lipids.

Magnesium stearate (Kebo, Sweden) was used as model lubricant.

Anhydrous silicon dioxide (Aerosil, Degussa AG, Germany) and talc (Kebo, Sweden) were used as anti-adherents.

PCMs were manufactured from cellulose using a special process involving mechanical treatment in the presence of water (WO 94/23703). The size fraction 0.71–1.17 mm was obtained by sieving.

Paracetamol and drug-and-lipid mixtures were incorporated into PCMs by the melting procedure as described in Example 1. The composition used contains 54% (w/w) cellulose, 43% (w/w) lipid (cetanol: paraffin 2:1) and 2.5% (w/w) paracetamol. The loading was performed in sub-batches of 150 g. Five subbatches were then poured into a polyethylene bag and mixed by hand shaking.

The porosity of pure PCMs was determined to be 54%. The porosity was calculated from pellet density data measured by mercury porosimetry and from apparent density data obtained by helium pycnometry.

Some of the drug-and-lipid loaded PCMs were mixed, for 60 minutes, with magnesium stearate, talc and/or anhydrous silicon dioxide in a Turbula Mixer (2 liters, W. A. Bachofen, Switzerland). The batch size of the mixtures was 50–100 g.

All materials were stored for no less than 48 hours at 40% relative humidity and room temperature (20–25° C.) before compaction. Loaded and empty PCMs were compressed to tablets, at 12 (±1), 20 (±1), 35 (±2), 50 (±2), 75 (±2), 100 (±5) and 200 (±5) MPa in a single punch press (Korsch EKO, Korsch, Germany). Flat faced punches with a diameter of 11.3 mm were used. The shortest distance between the punches was set to 3 mm. The particles for each tablet were weighed and poured manually into the die. A suspension of 1 % magnesium stearate in ethanol (95%) was used as an external lubricant. The tablets were kept at 40% relative humidity and room temperature (20–25° C.) for at least 48 hours, before characterisation.

Tensile Strength

The diametrical crushing force was measured in a tablet hardness tester (C 50, Holland Ltd., UK). Radial tensile strength was calculated from diametrical compression data according to the method by Fell and Newton (J. Pharm. Pharmacol., 20 (1968) 652–659). The results are shown in Table 2a for 12 MPa and 200 MPa pressures, respectively. The results are shown also in FIG. 1 which shows radial tensile strength vs. compaction pressure for tablets of PCMs with incorporated drug and lipids and unloaded PCMs. In FIG. 1, filled circles represent PCMs loaded with drug and lipid, and squares represent unloaded PCMs.

TABLE 2A

Tensile strengths for pellets compressed at 12 and 200 Mpa, respectively, with and without some additives.

| Additives | Radial tensile strength (MPa) | |
| --- | --- | --- |
| | Compressed at 12 MPa | Compressed at 200 MPa |
| No additives | 0.16 | 0.63 |
| 1% Mg stearate | 0.14 | 0.64 |
| 5% talc | 0.11 | 0.49 |
| 5% colloidal silicon dioxide | 0.094 | 0.53 |

TABLE 2A-continued

Tensile strengths for pellets compressed at 12 and 200 Mpa, respectively, with and without some additives.

| Additives | Radial tensile strength (MPa) | |
| --- | --- | --- |
| | Compressed at 12 MPa | Compressed at 200 MPa |
| 5% colloidal silicon dioxide and 1% magnesium stearate | 0.064 | 0.68 |

With reference to FIG. 1, surprisingly it was found that the incorporation of drug and lipid increases the compactability of the PCMs at low pressures, so that coherent tablets are obtained already at 12 MPa, whereby the tensile strength is above 0.1 MPa. The tensile strength increases approximately linearly with compaction pressure for empty PCMs. For drug-and-lipid PCMs, a constant tensile strength is obtained for pressures above 50 MPa. The increased tensile strength at low pressures of drug-and-lipid PCMs is probably due to the high ductility of the lipid mixture. That a lipid, added before compression by a melt method, may increase the tensile strength of tablets has been shown for stearic acid. The constant tensile strength at compaction pressures above 50 MPa could be due to the fact that no further deformation of the lipid is possible and that bonds have formed through all lipid material in the tablet. Some adherence of lipid material to the punch faces support the idea/suspicion that bonds may form due to partial melting or advanced diffusion during compaction. The assumption that bonds may have been formed is also supported by the low melting point of the lipids: 49.5° C. for cetanol and 50–62° C. for hard paraffin. Another explanation for the constant tensile strength above 50 MPa could be the fact that increased elastic expansion is cancelling out the effect of an increased volume reduction. The lipids appear to act as lubricants. It is not absolutely necessary to add magnesium stearate for the tablets to be ejected from the die. However, an antiadhesion agent may be needed in some instances.

Friability

For the purposes of this invention the friability of a compact member of the invention is defined as the amount of material attrited in a friabilator according to the procedure described below.

The friability of the tablets was measured in a friabilator model TA3 (Erweka Apparatebau, Germany). A pre-weighed sample of 10 tablets was rotated for 100 turns at a speed of 25 rpm and the amount of attrited material was determined gravimetrically. The friability expressed as a percentage was then calculated, and shown in Table 2b.

TABLE 2B

Friability values for pellets compressed at 12 and 200 MPa, respectively, with and without some additives.

| Additives | Friability (%) | |
| --- | --- | --- |
| | Compressed at 12 MPa | Compressed at 200 MPa |
| No additives | 2.1 | 0.27 |
| 1% magnesium stearate | 8.0 | 0.30 |
| 5% talc | 14 | 0.09 |
| 5% colloidal silicon dioxide | 100[1] | 0.38 |
| 5% colloidal silicon | 100[1] | 0.14 |

TABLE 2B-continued

Friability values for pellets compressed at 12 and 200 MPa, respectively, with and without some additives.

| | Friability (%) | |
|---|---|---|
| Additives | Compressed at 12 MPa | Compressed at 200 MPa |
| dioxide and 1% magnesium stearate | | |

[1]All tablet fragments were smaller than a half tablet after friability test

As can be seen from Table 2b, all tablets compressed at 200 MPa exhibit friability values well below 0.5%, and even at 12 MPa tablets without any additives exhibit friabilities of no more than 2.1%. For industrial applications and handling, it is desirable that the friability is less than 1%, although for certain applications higher friabilities may be acceptable.

Friction Properties

For evaluation of the friction, PCMs and mixtures of PCMs with additives was tableted in the single punch press at 12 and 200 MPa (±10%) with automatic feeding and at a rate of approx 37 tablets/minute. At least 25 tablets were compressed until constant ejection forces were obtained. The maximum upper and lower punch pressures and the ejection forces were then recorded for 10 tablets. The mean height of the tablets were measured after compression. The difference between maximum upper and lower punch pressures per tablet area in contact with the die (FD/A) and the ejection force per tablet area in contact with the die (EjF/A) were then calculated. These have been suggested as the most useful parameters for the study of friction during compaction. The height of the tablets after ejection was used as an estimate of height of the tablet in the die.

Table 3 shows the results of the evaluation of friction characteristics for different formulations.

TABLE 3

Friction characteristics and observed adhesion for pellets compressed at 12 and 200 MPa, respectively, with and without some additives.

| | EjF/A (kN/cm2) Compressed at | | FD/A (kN/cm2) Compressed at | | Observed adhesion (severe/ moderate/ |
|---|---|---|---|---|---|
| Additives | 12 MPa | 200 MPa | 12 MPa | 200 MPa | no) |
| No additives | 0.068[1] | 0.098[1] | 0.101 | 0.04 | severe |
| 1% magnesium stearate | 0.047[1] | 0.098[1] | 0.095 | 0.221 | moderate |
| 5% talc | 0.068[1] | 0.080[1] | 0.106 | 0.304 | no |
| 5% colloidal silicon dioxide | 0.297 | 0.313 | 0.280 | 0.712 | no |
| 5% colloidal silicon dioxide and 1% magnesium stearate | 0.137 | 0.153 | 0.192 | 0.638 | no |

[1]The ejection forces were not significantly distinguishable from the background inter-ference Disintegration The disintegration time in deionized water was measured in an Erweka ZT 3 (Erweka Apparatebau, Germany) according to the USP method with discs.

The in-vitro drug release rates were determined according to USP method II (paddle) in deionized water, at 37° C. with spectrophotometric detection. The stirring speed was 200 rpm. The USP method II (paddle) was used since preliminary trials showed that the tablets did not disintegrate if USP method I (basket) was used. However, in order to study the effect of tablet disintegration on drug release some tests using the basket method at 100 rpm were performed. One tablet or approximately 360 mg pellets were added to each vessel with 900 ml water. This amount was chosen in order to maintain sink condition during the experiment.

Figure 2:
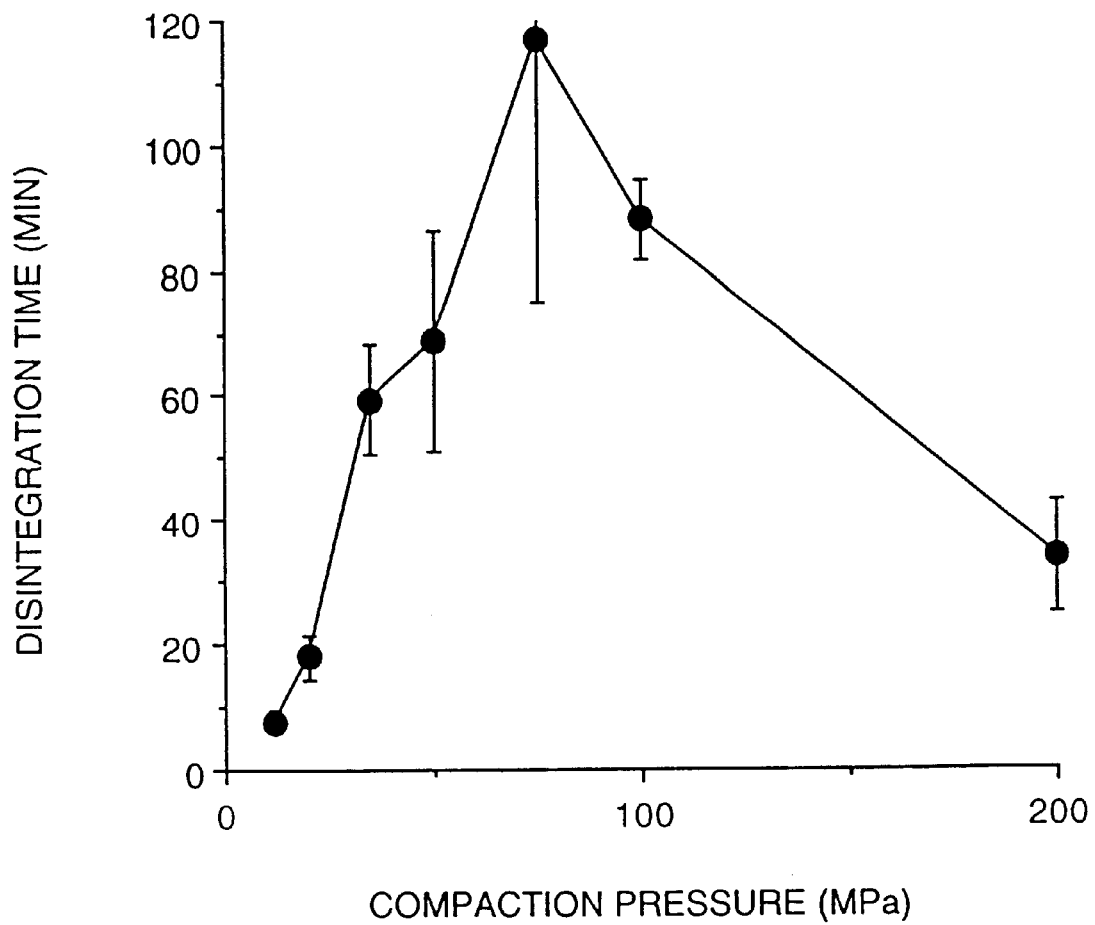
FIG. 2 is a graph showing disintegration time for tablets according to the invention as a function of compaction pressure.

Mean disintegration times were measured (Table 2c and FIG. 2), and was shown to be affected by compaction pressure. Thus, they vary between 8 and 120 minutes for PCMs without additives and between 6 and 65 minutes for PCMs with additives such as talc, magnesium stearate and/or colloidal silicon dioxide.

TABLE 2C

Disintegration times for pellets compressed at 12 and 200 MPa, respectively, with and without some additives.

| | Mean disintegration times (min) | |
|---|---|---|
| Additives | Compressed at 12 MPa | Compressed at 200 MPa |
| No additives | 8 | 34 |
| 1% magnesium stearate | 9 | 65 |
| 5% talc | 6 | 19 |
| 5% colloidal silicon dioxide | 9 | 29 |
| 5% colloidal silicon dioxide and 1% magnesium stearate | 7 | 25 |

From a medical point of view it is desirable that tablets exhibit disintegration times of less than about 240 minutes, and thus the tablets are well suited for their intended purpose. A maximum was observed at 75 MPa, and at higher and lower compaction pressures respectively, disintegration times were shorter. The decrease of disintegration time at compaction pressures above 75 MPa may be due to the cellulose fibres from different pellets getting into closer contact at higher pressures. Hence, more strain is caused by their swelling. Tablets made from unloaded PCMs disintegrated within less than 3 seconds irrespective of compaction pressure, demonstrating the good disintegrating effect of PCMs. Some small agglomerates of approximately 2–5 pellets could be observed also after disintegration of the tablets for drug-and-lipid PCMs but not for unloaded PCMs.

The tablets did not disintegrate when subjected to 100 rpm in the USP apparatus I (basket) as they did in the USP apparatus II (paddle) at 200 rpm (USP method II at 100 rpm caused a partial disintegration). After having been subjected to the basket method for 16 hours the tablets were still coherent although soft and swollen. The swollen tablets disintegrated immediately when gently pressed between the thumb and the index finger, indicating that in-vivo disintegration is probable.

Figure 4:
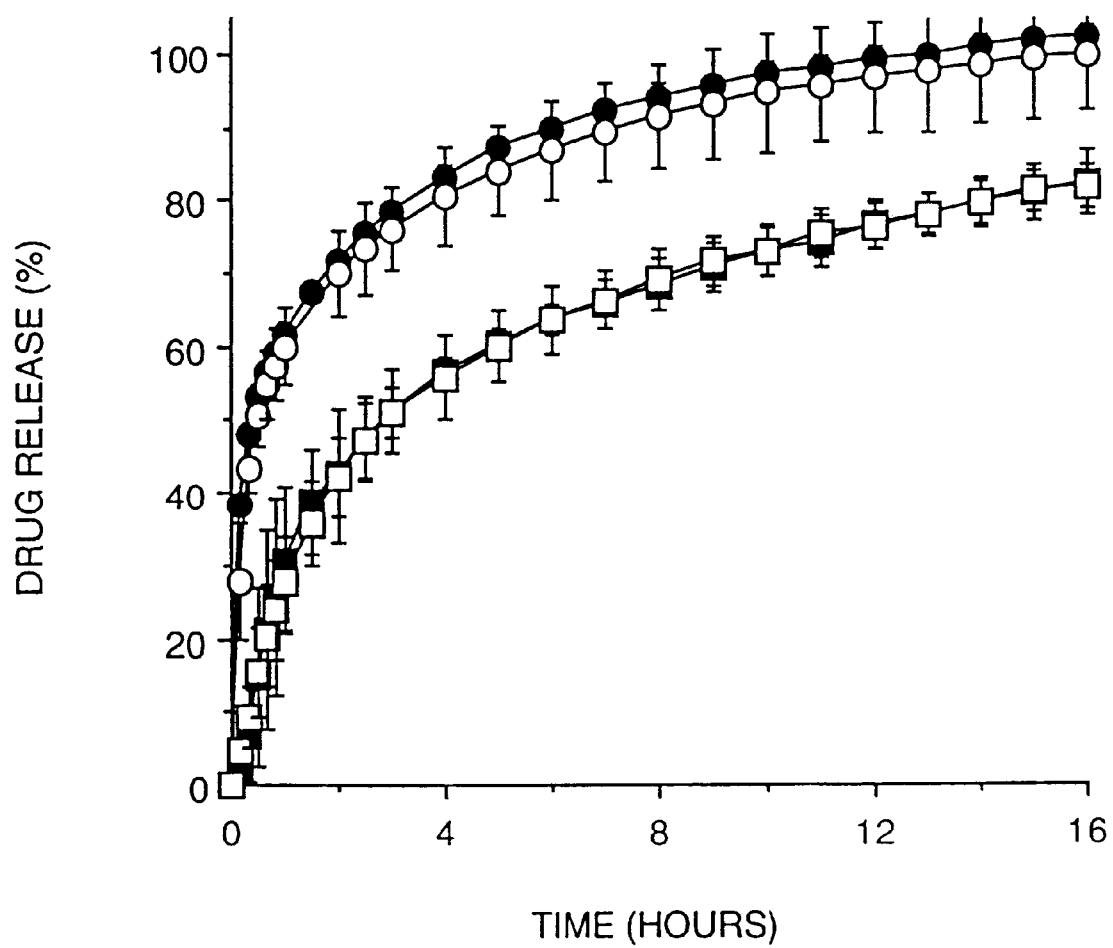
FIG. 4 is a graph showing release of drug from tablets according to the invention as a function of time at two different compaction pressures using two in-vitro dissolution methods.

Interestingly, there was no difference in drug release rate between the two different methods, indicating that the drug release is independent of tablet disintegration. The effect on release rate of compaction pressure and thus disintegration time, is shown in FIG. 4, by comparing the release rates using the two methods USP I (basket) at 100 rpm, and USP II (paddle) at 200 rpm. In FIG. 4 circles represent tablets compressed at 12 MPa and tested in USP apparatus II (filled circles), and the same tablets tested in USP apparatus I (empty circles), respectively. Squares represent tablets compressed at 200 MPa and tested in USP apparatus II (filled) and USP apparatus I (empty), respectively.

Without wishing to be bound by any theory, it is believed that the reason for this may be that pores are rapidly formed between the pellets when the cellulose swells and that the transport in these pores is so rapid that only the diffusion in the pellets will control the release rate. The bonds keeping the swollen tablet coherent may be working over a surface area which is negligible compared to the exposed surface area of the pellets. Hence, the breaking of the bonds does not influence the drug release rate. However, there may still be bonds over larger surface areas, forming small agglomerates of pellets. These bonds may influence the release rate but they are not necessarily broken during the disintegration of the tablet but may remain unchanged throughout the dissolution process.

Drug Release

Figure 5:
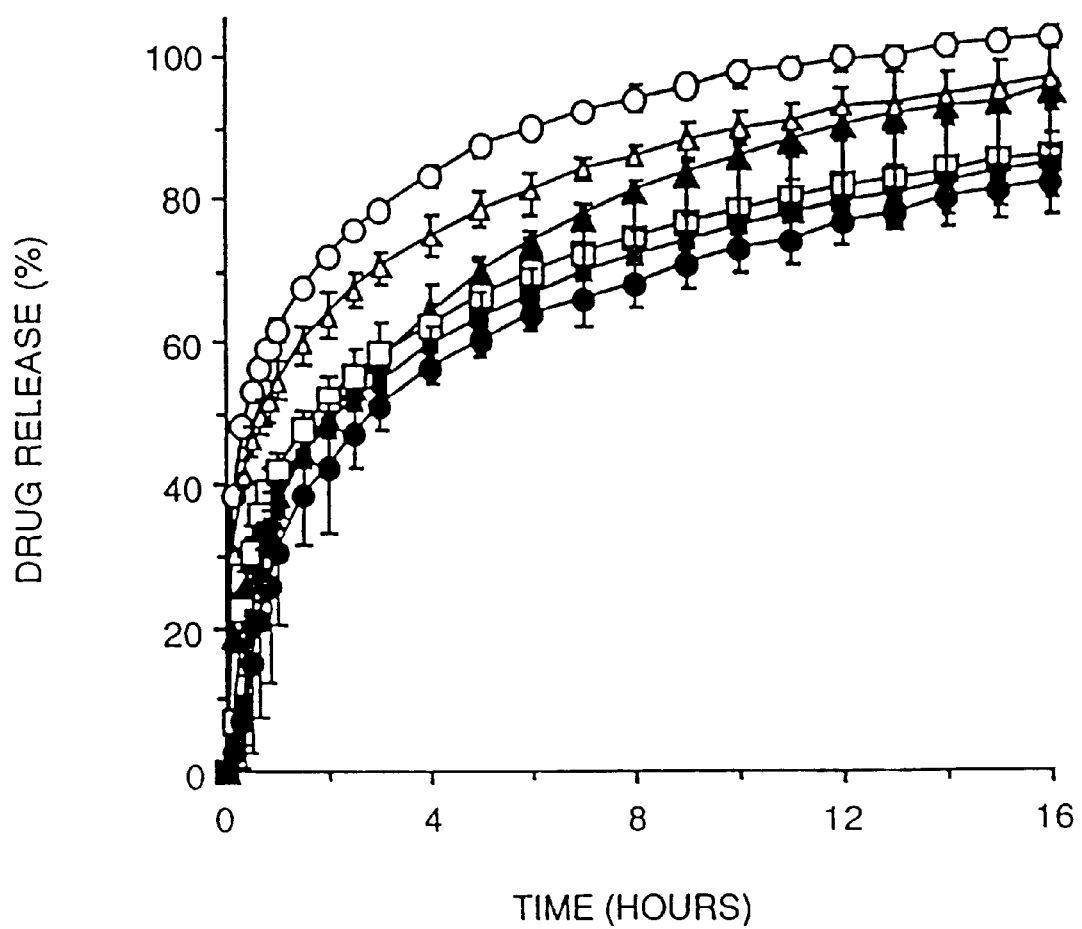
FIG. 5 is a graph showing release of drug for tablets according to the invention as a function of time at five different compaction pressures.

The drug release from tablets compacted at 12 MPa was faster than from uncompressed pellets. The increase in release rate at 20 MPa was less and at 35 MPa the release was slower than for uncompacted pellets. Further increase in the compaction pressure increased the release rate only to a small extent. This is shown in FIG. 5 wherein release rates for tablets compressed at various pressures are shown as a function of time. The tests were performed using the USP II method at 200 rpm. In FIG. 5, empty circles and empty triangles represent tablets compressed at 12 MPa and 20 MPa, respectively. Empty squares and filled squares represent tablets compressed at 35 MPa and 100 MPa, respectively. Filled circles and filled triangles represent tablets compressed at 200 MPa and uncompressed pellets, respectively.

Again without wishing to be bound by any specific theory, it is possible that the increase in release rate at low pressures may be due to some lipid being squeezed out of the PCMs during compression, increasing the porosity and surface area of the pellets. At higher compaction pressures, lipid may be squeezed back into the pores of the PCMs. In this process, some of the drug is redistributed and less drug may be exposed at the surfaces of the PCMs. It has been shown that the incorporation process may cause a higher drug concentration close to the surface of the PCMs than in the centre of the matrices. It is also possible that higher compaction pressures may increase the number of small agglomerates of spheres, which do not deagglomerate upon tablet disintegration. Consequently, the surface area of the matrices will decrease.

For pure pellets or mixtures with magnesium stearate or talc, the lower punch forces detected during the ejection were not significantly different from the background reference (Table 3). When colloidal silicon dioxide was added the ejection force (EjF) increased. An addition of 1% magnesium stearate to the silicon dioxide mixture decreased the ejection force somewhat. As expected, FD/A values were low for pure pellets compacted at both 12 and 200 MPa Addition of magnesium stearate or talc did not increase FD/A. Colloidal silicon dioxide, on the other hand, increased FD/A. This indicates that no lubricant is needed for the tableting of extended release pellets prepared by the incorporation of lipid release modifiers into PCMs. However, since some adherence to punch faces was seen, addition of an antiadherent may be necessary. If so, talc gives better friction properties than colloidal silicon dioxide when added at the same concentration.

Addition of excipients (magnesium stearate, talc and/or colloidal silicon dioxide) decreased the tensile strength of the tablets compacted at 12 MPa (Table 2a).

For tablets compressed at 200 MPa the effect of additions of excipients on tensile strength was small. It is contemplated, without knowing the exact mechanism, that the lack of effect of excipients on tensile strength at higher compaction pressure may be due to the high ductility of the lipids, which means that the lipids could flow around the excipient particles and create bonds around them. It is well known that a high tendency of a substance to fragment during compaction will counteract the tensile strength, lowering effect of magnesium stearate. However, it seems reasonable that extreme ductility may have the same effect. Extreme deformation of a substance will lead to redistribution of the magnesium stearate covering its surfaces.

The effect on disintegration times of the added excipients was low at 12 MPa. At 200 MPa the disintegration time was increased by magnesium stearate and decreased by talc. The increase in disintegration time, when magnesium stearate is added, is expected due to the hydrophobic nature of this substance while an explanation for the decrease seen when talc is added is less obvious.

The friability of tablets with no additives and compressed at 12 MPa was 2.1%. Addition of excipients (especially colloidal silicon dioxide) increased the friability considerably. At 200 MPa the friability of pure pellets and all investigated mixtures was below 0.5% which indicates a sufficient tablet strength for industrial handling.

Addition of magnesium stearate and talc did not affect the release rate from tablets compressed at 12 MPa. A small increase in the release rate was seen when colloidal silicon dioxide was added. At 200 MPa all additions gave an increase of the release rate. The increase in the release rate was highest for 5% colloidal silicon dioxide and 5% colloidal silicon dioxide+1% magnesium stearate. The increase was smaller when 1% magnesium stearate was added. For all three mixtures containing silicon dioxide and/or magnesium stearate, the release rate was faster than from the uncompressed pellets. The release from tablets without additives was slower than from uncompressed pellets.

Figure 6:
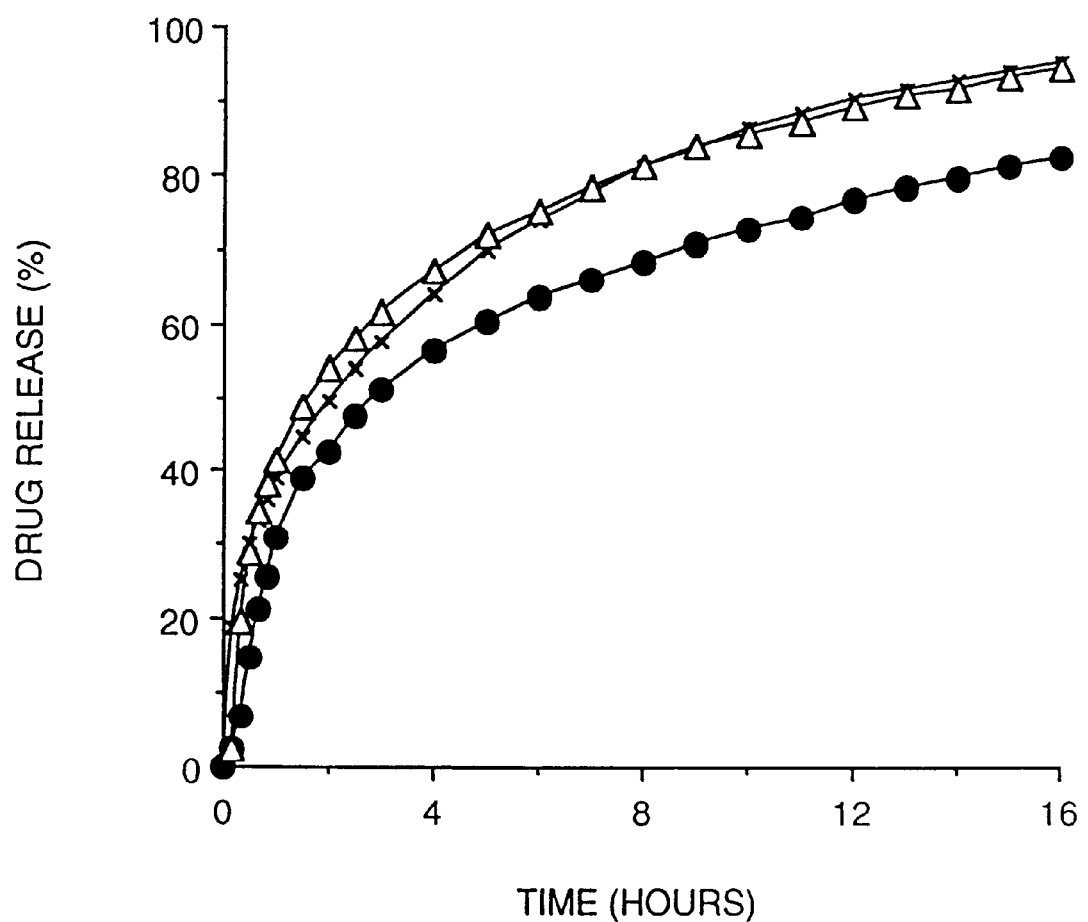
FIG. 6 is a graph showing the effect of talc on release of drug of a tablet according to the invention.

Surprisingly, the release rate from tablets containing an active drug (paracetamol), with and without added talc (5% w/w) was approximately the same as from uncompressed pellets. This effect is shown in FIG. 6, wherein filled circles represent tablets without talc and compressed at 200 MPa. Empty triangles represent tablets with talc and compressed at 200 MPa Crosses represent uncompressed pellets without talc. This suggests that it is possible to produce extended release multiple-unit tablets from drug-and-lipid PCMs with only a small amount of additives.

The higher release rate in the presence of additives may be due to the added substances forming a coating layer around the pellets. This coating layer may then either prevent the formation of non-disintegrating agglomerates or influence the redistribution of drug particles during compression. Another possible explanation for the increased release rate is that hydrophilic additives are pressed into the matrix pellets thereby increasing their hydrophilicity. This may be a possible mechanism for silicon dioxide but seems less probable for talc and magnesium stearate.

Thus, in accordance with the invention, extended release matrix pellets prepared by incorporation of release modifiers, especially lipids, into PCMs can be compacted into disintegrating tablets without the addition of any excipients. The release rate is increasing at low compaction pressures and decreasing at higher pressures. By addition of 5% talc it is possible to achieve the same release profile from tablets compacted at 200 MPa as from uncompacted pellets. The disintegration times appear to be relatively long at higher pressures but on the other hand, drug release appears to be independent of tablet disintegration. The pellets seem to be self lubricating although an addition of antiadherent may be necessary.

What is claimed is:

1. A method of providing a multiple unit preparation in the gastrointestinal system of an individual for extended release of an active compound, comprising orally administering to the individual a compact member having a friability of less than 2.1% and a disintegration time in-vitro, measured with the USP method with discs, of less than about 240 minutes, the compact member comprising a plurality of porous cellulose matrices (PCMs) having the active compound and a release-modifying agent comprising a lipid in the pores thereof, the compact member disintegrating in the gastrointestinal system to provide a multiple unit preparation.

2. The method according to claim 1, wherein after disintegration of the compact member, the PCMs have substantially the same release characteristics as noncompacted PCMs having the active compound and the release-modifying agent located in the pores thereof.

3. The method according to claim 1, wherein the friability of the compact member is less than 1%.

4. The method according to claim 1, wherein the friability of the compact member is less than 0.5%.

5. The method according to claim 1, wherein the disintegration time in-vitro of the compact member is less than 90 minutes.

6. The method according to claim 1, wherein the disintegration time in vitro of the compact member is less than 60 minutes.

7. A method of administering an active compound in a compact member having a disintegration time in-vitro, measured with the USP method with discs, of less than about 240 minutes and a friability of less than 2.1% to provide extended release of the active compound, comprising administering a compact member prepared by a compacting process, capable of disintegration after oral administration, and adapted to provide extended release of the active compound contained therein, the compact member comprising a plurality of porous cellulose matrices (PCMs), wherein a) the active compound and a release-modifying agent comprising a lipid are located in the pores of the PCMs;

b) the friability of the compact member is less than 2.1%; and c) the disintegration time in-vitro, measured with the USP method with discs, of the compact member is less than about 240 minutes.

8. The method according to claim 1, wherein the lipid is selected from the group consisting of fatty acids, long chain alcohols, naturally occurring and synthetic waxes, glyceryl esters of fatty acids, aliphatic hydrocarbons, polyglycerol esters of fatty acids, and any mixture thereof.

9. The method according to claim 8, wherein the lipid is selected from the group consisting of stearic acid, cetostearyl alcohol, glyceryl monostearate, glyceryl distearate, glyceryl tristearate, hard paraffin, and mixtures thereof.

10. The method according to claim 1, wherein up to about 10% by weight of talc is incorporated in the compact member.

11. The method according to claim 10, wherein up to 5% by weight of talc is incorporated in the compact member.

12. The method according to claim 1, wherein the compact member is formed from a composition comprising up to 1% by weight of a lubricant.

13. The method according to claim 12, wherein the lubricant comprises magnesium stearate.

14. The method according to claim 1, wherein the radial tensile strength of the compact member is higher than about 0.1 MPa.

15. The method according to claim 14, wherein the radial tensile strength of the compact member is higher than 0.5 MPa.

16. The method according to claim 1, wherein the compact member comprises up to 2.5% by weight of the active compound.

17. The method according to claim 1, wherein the compact member comprises not more than about 10% of additives therein.

18. A method of manufacturing a compact member having a disintegration time in-vitro, measured with the USP method with discs, of less than about 240 minutes and a friability of less than 2.1% and being adapted to provide extended release of an active compound, the method comprising a) exposing a plurality of porous cellulose matrices (PCMs) to an active compound and a release-modifying agent, comprising a lipid in optional sequence or mixture, for a time sufficient for the active compound and the release-modifying agent to fill the pores in the PCMs to a preselected level; and b) compacting the PCMs comprising the active compound and the release-modifying agent to a desired shape to provide a compact member adapted to provide extended release of the active compound and having a friability of less than 2.1% and a disintegration time in-vitro, measured with the USP method with discs, of less than about 240 minutes.

19. The method according to claim 18, wherein the pressure in the compacting step is less than about 500 MPa.

20. The method according to claim 19, wherein the pressure in the compacting step is in the range of from 10 up to 200 MPa.

21. The method of claim 7, wherein after disintegration of the compact member, the PCMs have substantially the same release characteristics as noncompacted PCMs having the active compound and the release-modifying agent located in the pores thereof.

* * * * *

UNITED STATES PATENT AND TRADEMARK OFFICE
CERTIFICATE OF CORRECTION

PATENT NO.   : 6,322,813 B1
DATED        : November 27, 2001
INVENTOR(S)  : Torkel Gren et al.

It is certified that error appears in the above-identified patent and that said Letters Patent is hereby corrected as shown below:

Column 14,
Line 33, change "agent, comprising a lipid" to -- agent comprising a lipid, --.
Line 35, after "agent", insert -- comprising a lipid --.

Signed and Sealed this

Twenty-fourth Day of December, 2002

JAMES E. ROGAN
*Director of the United States Patent and Trademark Office*